United States Patent [19]

Ngo

[11] Patent Number: 4,886,755

[45] Date of Patent: Dec. 12, 1989

[54] PREPARATION OF POLYMERIC THIOL GELS FOR COVALENT BONDING OF BIOLOGICALLY ACTIVE LIGANDS

[75] Inventor: That T. Ngo, Irvine, Calif.

[73] Assignee: Bioprobe International, Inc., Tustin, Calif.

[21] Appl. No.: 110,103

[22] Filed: Oct. 13, 1987

Related U.S. Application Data

[63] Continuation of Ser. No. 679,167, Dec. 7, 1984, abandoned.

[51] Int. Cl.$^4$ .................. C12N 9/00; C12N 11/06; G01N 33/547; C07K 17/06
[52] U.S. Cl. .................. 435/183; 435/178; 435/180; 435/181; 435/814; 436/529; 436/531; 436/532; 525/54.1; 530/813; 530/815; 530/816; 536/1.1; 536/54
[58] Field of Search .............. 435/177, 178, 179, 180, 435/181, 183, 814; 436/529, 531, 532; 536/1.1, 51, 54; 525/54.1, 54.11; 530/813, 815, 816

[56] References Cited

U.S. PATENT DOCUMENTS 4,415,665  11/1983  Mosbach ........................ 435/179
4,582,875  4/1986  Ngo ............................ 435/178 X

OTHER PUBLICATIONS

R. Axen et al., *Acta Chem. Scand.*, B 29:471–474 (1975).
K. Nilsson et al., *Biochem Biophys. Res. Comm.*, 102:449–457 (1981).
K. Nilsson et al., *Eur. J. Biochem.*, 112:397–402 (1980).
T. Mukaiyama et al., *Chem. Lett.*, 1159–1162 (1975).
J. Carlsson et al., *Acta Chem. Scand.*, B30-180-182 (1976).
K. Hojo, et al., *Chem. Lett.*, 437–440 (1977).
Porath et al., "Immobilized Enzymes. Methods in Enzymology", (Mosbach, K., Ed.), vol. 44, pp. 19–45, Academic Press, New York (1976).
Ellman, *Arch. Biochem. Biophys.* 82:70–77 (1959).

*Primary Examiner*—David M. Naff
*Attorney, Agent, or Firm*—Nilsson, Robbins, Dalgarn, Berliner, Carson & Wurst

[57] ABSTRACT

Thiol gels are prepared from hydroxyl containing polymers by forming a 2-fluoro-1-methylpyridoxy derivative of the polymer followed by reacting the derivative with sodium dimethyldithiocarbamate and reducing to produce a sulfhydryl substituted polymer. Alternatively, the derivative is reacted with dithiothreitol to produce a sulfhydryl substituted polymer having free sulfhydryl groups spaced from the polymer. The thiol gel can be activated by means of 2,2'-dipyridyl disulfide and reacted with a free sulfhydryl containing biologically active ligand in order to provide an insolubilized ligand which can be used for various purposes including use as an immobilized biologically active material or use as a matrix in covalent chromatography.

8 Claims, 3 Drawing Sheets

PREPARATION OF POLYMERIC THIOL GELS FOR COVALENT BONDING OF BIOLOGICALLY ACTIVE LIGANDS

This application is a continuation of Ser. No. 679,167, filed Dec. 7, 1984, now abandoned.

BACKGROUND AND SUMMARY OF THE INVENTION

This invention relates to derivatives of polymers which are useful as covalent chromatographic matrices. In one of its more particular aspects this invention relates to the preparation of such derivatives.

The need for purifying various biologically active materials in a facile manner has long been appreciated. Early methods of enzyme purification, for example, were cumbersome and time consuming. Recently it has been found that enzymes and other biologically active materials can be purified by a process which involves immobilization of the enzyme or other biologically active material which will be referred to herein as a ligand, followed by separation of the immobilized ligand from the mixture in which it is present. The ligand can then be used in its immobilized form, if desired, or can be released from the carrier on which it is immobilized by suitable chemical treatment and used in its non-immobilized form. The discovery of methods for covalently bonding ligands to polymeric carriers has advanced the practice of enzymology, immunology, and various other biological techniques.

One of the first methods for immobilizing biological ligands involved treatment of a polymer containing hydroxyl groups with an activating agent such as cyanogen bromide, CNBr. The activated polymer could then be used to directly bind various biological ligands to the polymer by means of covalent bonds. Porath et al. describe several chemical activation methods including the CNBr method in Porath, et al., "Immobilized Enzymes. Methods in Enzymology," K. Mosbach, Ed., Vol. 44, p. 19-45, Academic Press, New York (1976). Most of the early methods for activating polymers containing hydroxyl groups were subject to certain disadvantages which made their widespread use impractical. In particular CNBr activation procedures suffer from the following disadvantages: (1) the linkages formed between CNBr-activated hydroxyl containing polymers and the amino groups of ligands which are reacted with the activated polymers are labile; (2) the reaction between the activated polymer and ligand frequently results in the introduction of charged species which interfere with utilization of the reaction product in affinity absorption; (3) CNBr is a noxious, lachrimatory and poisonous chemical which requires special care in its handling.

Efforts to find another method other than the CNBr method for coupling ligands to hydroxyl containing polymers resulted in the use of a number of different reagents including triazine trichloride, N-hydroxy succinimide, 1,1'-carbonyldiimidazole and epoxy compounds. The use of epoxy compounds is described in Axen et al. Acta Chem. Scand B29: 471-474 (1975). Epichlorohydrin or 1,4-bis(2,3-epoxypropoxy) butane reacts with a hydroxyl group of an agarose gel to form an epoxide gel. The epoxide gel is then reacted with sodium thiosulfate to give a thiosulfate ester gel, which is then reduced by dithiothreitol to give a modified agarose gel containing a thiol group. This so-called thiol gel is then converted to a 2-pyridyl disulfide gel by means of 2,2'-dipyridyl disulfide. A solution of urease is then passed through a column of the disulfide gel to obtain an enzyme conjugate of high protein content and high catalytic activity. One disadvantage of this procedure is that the epoxy substituted polymer is not stable enough to store.

More recently the use of various organic sulfonates has found wide use in preparing immobilized affinity ligands. For example, Nilsson et al., *Eur. J. Biochem.*, 112: 397-402 (1980) describes the coupling of a number of biomolecules to agarose gels by means of p-toluenesulfonyl chloride. The biomolecules used include nucleic acids and enzymes.

The use of other organic sulfonyl halides and the use of other hydroxyl group carrying supports are described in Nilsson et al., *Biochem. Biophys. Res. Comm.*, 102: 449-457 (1981). The most active sulfonyl halide appears to be 2,2,2-trifluoroethanesulfonyl chloride (tresyl chloride). Other hydroxyl group carrying supports mentioned in this reference are cellulose, diol-silica, glycophase-glass, and hydroxyethyl methacrylate.

U.S. Pat. No. 4,415,665 to Mosbach et al. teaches a method of covalently binding a biologically active substance containing amino, thiol or aromatic hydroxyl groups directly to a polymeric substance containing at least one hydroxyl group by forming a reactive sulfonate derivative of the polymeric substance and then reacting the thus activated polymeric substance directly with the biologically active organic substance. Although the use of sulfonyl halides has proven to be advantageous in many ways, the cost of the more active organic sulfonyl halides tends to be prohibitive and tresyl chloride, being a liquid, is less convenient to handle.

The purification of enzymes using consecutive thiol-disulfide interchange reactions is described in Carlsson et al., *Acta Chem. Scand.*, B30: 180-182 (1976) in a communication in which urease is covalently bonded to agarose-2-pyridyl disulfide. Although this procedure is effective in carrying out the covalent chromatographic purification of urease, the preparation of the agarose-2-pyridyl disulfide involves a combination of steps utilizing an unstable epoxide derivative.

Mukaiyama et al. disclose the use of 1-methyl-2-alkoxypyridinium salts as reagents for preparing various 2-pyridyl sulfides. Mukaiyama et al., *Chem. Lett.*, 1159-1162 (1975).

Hojo et al. successfully demonstrated the conversion of various alcohols to the corresponding thioalcohol by reacting the alcohol with 1-methyl-2-fluoropyridinium salts and sodium N,N-dimethyldithiocarbamate followed by reductive cleavage. The alcohols exemplified by these authors, including carbohydrates and steroids, were low molecular weight monomeric alcohols. *Chem. Lett.*, 437-440 (1977).

A convenient method has now been found for preparing covalent chromatographic matrices utilizing a hydroxyl containing polymer which has been activated by reaction with 2-fluoro-1-methylpyridinium toluene-4-sulfonate (FMP). The preparation and use of the activated hydroxyl containing polymer in forming covalent bonds with various ligands containing amino and sulfhydryl groups has been described in my copending application Ser. No. 679,525 filed of even date herewith, now U.S. Pat. No. 4,582,875, the disclosure of which is incorporated herein by reference. However, the covalently bound ligands are difficult to remove from the polymeric matrix. Therefore, it was found desirable to bind the ligand to the polymer in a manner such that the ligand could be readily removed when desired. The procedure involves conversion of the activated polymer to a thiol gel, that is, a sulfhydryl group containing polymer. The thiol gel can then be reacted with 2,2'-dipyridyl disulfide to form a 2-pyridyl disulfide derivative of the polymer. Thiol-disulfide interchange with the sulfhydryl group containing ligand causes the ligand to be linked to the polymer by means of a disulfide linkage. Removal of the ligand when desired can be readily accomplished by reduction of the disulfide linkage with a thiol such as dithiothreitol.

Two different routes to the thiol gel are available. In one, sodium dimethyl dithiocarbamate is used to convert the activated polymer to the corresponding dimethyl dithiocarbamyl derivative, which, by means of reductive cleavage is converted to the desired sulfhydryl substituted polymer, hereinafter referred to as the DS-gel.

Another route to a thiol gel involves treatment of the FMP activated polymer with dithiothreitol to form a dithiothreityl gel, a thiol gel, hereinafter referred to as the DTT-gel, in which the free sulfhydryl group is 4 carbon atoms removed from a thioether linkage to the polymer.

Depending upon the particular application for which the covalent chromatographic matrix is intended, either the DS-gel or the DTT-gel may be ideally suited for the particular chromatographic procedure which is to be carried out. For example, the DTT-gel may be particularly adapted for use in those instances where the ligand contains bulky groups which might prevent it from approaching close enough to the polymer to attack the disulfide linkage, were it not for the space provided between the polymer surface and the disulfide linkage by the intervening 4 carbon atom chain.

DETAILED DESCRIPTION

Figure 1:
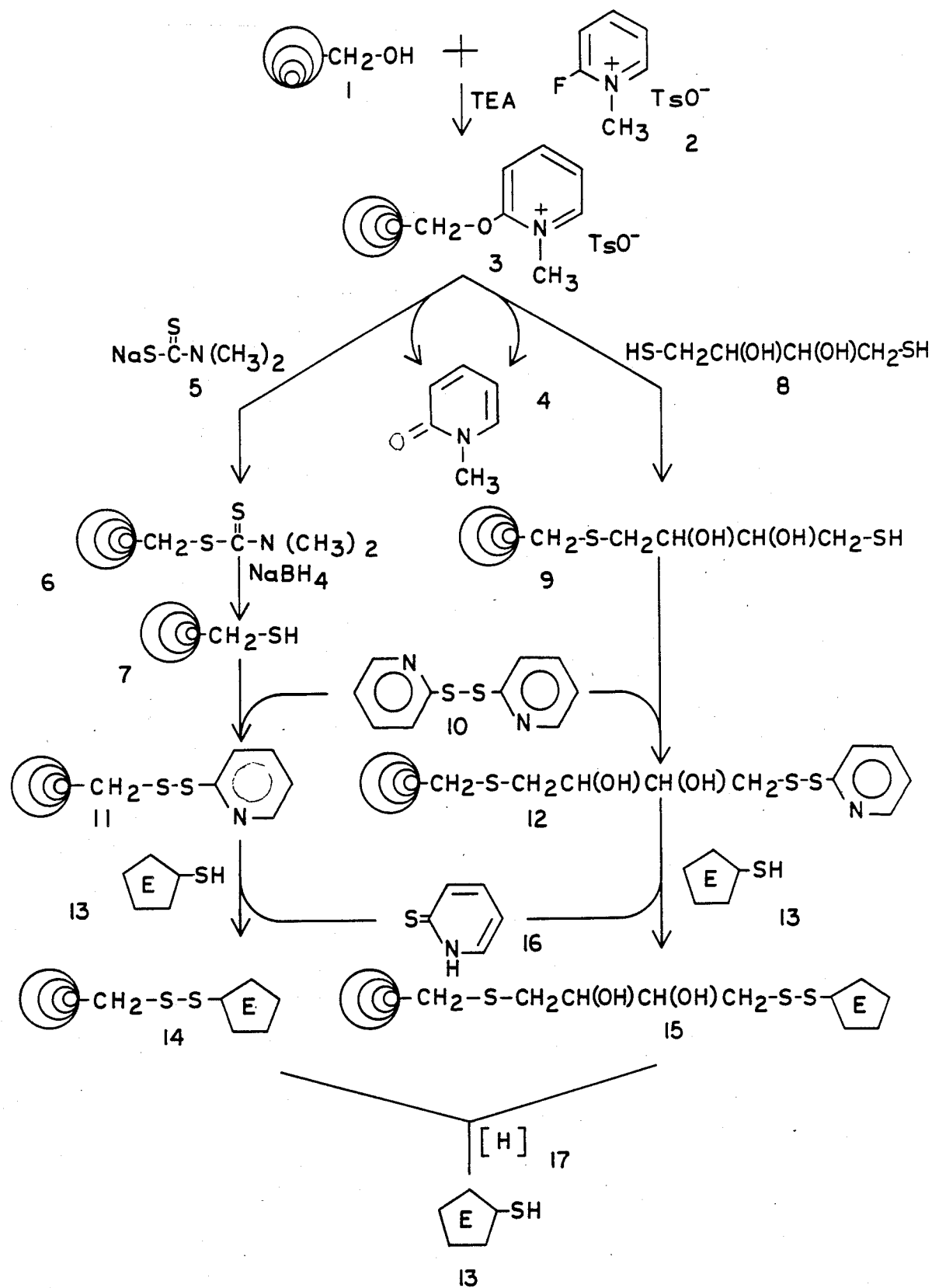
FIG. 1 is a schematic flow sheet illustrating the present invention.

The present invention provides the means for immobilizing and covalently chromatographing a wide variety of biological ligands. Suitable ligands are those which contain a free sulfhydryl group or those into which sulfhydryl groups can be introduced by chemical synthetic means. Many different types of biological materials can therefore be used in the application of the thiol gel process of the present invention. Such ligands include enzymes, nucleoproteins, antigens, antibodies, haptens, hormones, vitamins, polypeptides and other compounds of biological interest.

The invention will be described in detail with reference to FIG. 1, wherein there are shown the various steps involved in the overall reaction scheme.

The first step in the process is the reaction of a hydroxyl containing polymer having at least one reactive hydroxyl group (Formula 1) with 2-fluoro-1-methyl-pyridinium toluene-4-sulfonate (Formula 2). Many polymeric materials can be used so long as they contain at least one reactive hydroxyl group. Principal among the polymers which may be used are the polysaccharides, such as the celluloses, dextrans, cross-linked dextrans, agaroses, cross-linked agaroses, sepharoses, cross-linked sepharoses, sephadexes and cross-linked sephadexes. Other polymeric materials which can be used include natural, semi-synthetic and synthetic materials containing hydroxyl groups such as polyethylene glycol, polyvinyl alcohol, polyhydroxymethyl methyl acrylate, glycophase glass and silica particles having bonded groups containing at least one hydroxy group bonded to a carbon atom. Hereinafter the polymer will sometimes be referred to as a gel. The polymer may be provided in the form of beads, if desired, or in any other convenient form. Other 2-halo-1 methylpyridinium salts such as 2-chloro-1-methylpyridinium salts can be used, but the 2-fluoro-1-methylpyridinium salts are preferred because of their greater reactivity. The reaction between the hydroxyl containing polymer and FMP or other 2-halo-1-methylpyridinium salt can be conducted in any polar organic solvent such as acetonitrile, acetone or tetrahydrofuran in the presence of a base such as a tertiary amine, for example, triethylamine (TEA) or tributylamine (TBA). Under mild conditions of ambient temperature and pressure the reaction between the hydroxyl containing polymer and FMP takes place rapidly and smoothly, going to completion in about 1–15 minutes. The resulting 2-alkoxy-1-methylpyridinium salt (Formula 3) will be referred to at times as the activated polymer or activated gel. The activated polymer is readily attacked by nucleophiles, since the 1-methyl-2-pyridoxy group is a good leaving group being readily converted to 1-methyl-2-pyridone (Formula 4) upon nucleophilic substitution by a ligand.

One sequence of reactions leading to the production of a thiol gel, wherein the sulfhydryl group is directly bonded to a carbon atom of the polymer, utilizes sodium dimethyl dithiocarbamate (Formula 5) to react by nucleophilic substitution upon the activated polymer to produce a dimethyl dithiocarbamyl derivative of the polymer (Formula 6). Reaction of the activated gel with sodium dimethyl dithiocarbamate occurs readily in an organic solvent such as N,N-dimethyl formamide (DMF). Other solvents which may be used include acetonitrile, acetone and tetrahydrofuran. The reaction is readily conducted under ambient conditions of temperature and pressure in a period of about 12 to 20 hours.

Reduction of the dimethyl dithiocarbamyl derivative of the gel results in a thiol gel having a sulfhydryl group directly bonded to a carbon atom of the gel (Formula 7). Reduction can be readily accomplished using any standard reducing agent such as sodium borohydride, lithium aluminum hydride or sodium dithionite. The reaction takes place readily under ambient conditions of temperature and pressure and in a period of time of about 6 hours to 12 hours. The resulting DS-gel has a sulfhydryl group content of 5–15 micromole per gram of dry gel.

Another route to a thiol gel involves the reaction of the activated gel (Formula 3) with dithiothreitol (FORMULA 8) to produce the DTT-gel, (FORMULA 9) a thiol gel having a sulfhydryl group, which is separated by a 4 carbon atom chain from a thioether linkage to the polymer. The activated gel and dithiothreitol are readily reacted by mixing in the presence of a base such as sodium bicarbonate or a tertiaryamine, such as triethylamine or tributylamine. The reaction is conducted under ambient conditions of temperature and pressure and is complete in a period of about 4 to 8 hours.

The resulting DTT-gel, like the DS-gel, can then be used as a covalent chromatographic matrix. However, before proceeding with the use thereof, it is important that any unreacted 1-methylpyridoxy activating groups be removed from the DS-gel or DTT-gel in order to control the desired course of the reaction with the ligand which is the subject of the covalent chromatography. Removal of unreacted activating groups is readily accomplished by using a reactive ligand such as Tris-HCl, for example, 0.2M Tris-HCl, pH 9, ethanolamine, mercaptoethanol, or other suitable reactive ligand which will not, however, react with the sulfhydryl group of the thiol gel.

The thiol gel is activated in order to conduct the thiol-disulfide interchange which is responsible for the binding of the desired ligand to the gel. Activation is most readily achieved by reacting the thiol gel with 2,2'pyridyl disulfide (Formula 10). The reaction proceeds under ambient conditions of temperature and pressure and is complete in a period of about 1 to 3 hours.

The activated DS-gel (Formula 11) or the activated DTT-gel (Formula 12) is then reacted with the desired ligand, represented in FIG. 1 as an enzyme having a free sulfhydryl group (Formula 13) in order to form a disulfide linkage between the gel and the enzyme. In the case of the DS-gel, the disulfide linkage binds the enzyme directly to a carbon atom of the gel (FORMULA 14), whereas in the case of the DTT-gel, the disulfide linkage binds the enzyme to a 4 carbon atom chain linked by a sulfur atom to a carbon atom of the gel (Formula 15). In both cases, 2-thiopyridone (Formula 16) is displaced from the activated thiol gel. Formulae 14 and 15 illustrate immobilized enzymes. It should be appreciated that many other ligands can be similarly immobilized in accordance with the above described process. Reaction of the ligand with the activated thiol gel is readily carried out under ambient conditions of temperature and pressure with suitably purified and buffered ligand. The reaction is complete in about 2 to 6 hours.

The immobilized enzyme will release the enzyme (Formula 13) upon treatment with a reducing agent (Formula 17) such as cysteine, dithiothreitol or mercaptoethanol. Release of the enzyme occurs readily at ambient conditions of temperature and pressure.

The invention will be better understood with reference to the following examples which are intended for purposes of illustration and are not to be construed as in any way limiting the scope of the present invention, which is defined in the claims appended hereto.

EXAMPLE 1

Preparation of FMP-Activated gel

Sepharose CL-4B was washed successively with 20 gel volumes of distilled water and acetone water mixtures having volume ratios of 25:75, 50:50, 75:25 and pure acetone, and finally with 10 gel volumes of dry acetone. A quantity of 50 grams of the gel was suspended in 50 ml dry acetonitrile, mixed with 1 ml dry triethylamine and stirred vigorously at room temperature. A solution of 3 grams 2-fluoro-1-methylpyridinium toluene 4-sulfonate (FMP) in 40 ml dry acetonitrile and 1.5 ml dry triethylamine was added to the gel suspension in 5 ml portions. Ten minutes later, the gel was washed with 10 gel volumes of acetone and mixtures of acetone with 2 mM HCl in ratios of 75:25, 50:50, 25:75, and 100% 2 mM HCl and stored dry.

EXAMPLE 2

Preparation of Thiol Gel-dimethyl dithiocarbamate method (DS-Gel)

A 1 g sample of the dry activated gel of Example 1 was washed with 100 ml dry N,N-dimethylformamide (DMF) and added to 100 ml DMF containing 1.8 g sodium dimethyl dithiocarbamate. The gel suspension was stirred at room temperature for 16 hours, then washed with 100 ml dry DMF and resuspended in 50 ml dry DMF. Sodium borohydride was added to the suspension in the amount of 380 mg. The gel was continuously stirred at room temperature for 4 hours. Then another 380 mg sodium borohydride was added. The suspension was stirred at room temperature for 4 more hours and then the gel was washed with 200 ml DMF, 1000 ml 2 mM HCl, 500 ml 0.5N NaCl and 500 ml 2 mM HCl. The sulfhydryl content of the thiol gel was determined by means of 5,5'-dithiobis (2-nitrobenzoic acid) as described in G. L. Ellman, Arch. Biochem. Biophys, 82:70-77 (1959) and determined to be 9 micromole/g of dry gel.

EXAMPLE 3

Preparation of thiol gel-dithiothreitol method (DTT-GEL)

The dry activated gel of Example 1 in a quantity of 1 gram was added to a stirred solution of 1M dithiothreitol (DTT) in 0.2 M NaHCO$_3$. The suspension was stirred at room temperature for 5 hours. The gel was then washed with 500 ml 0.2M NaHC0$_3$, 500 ml distilled water and 1000 ml 2 mM HCl. The sulfhydryl content of the gel was found to be 6 micromole /g of dry gel.

EXAMPLE 4

Preparation of Activated Thiol Gel.

The DS- gel of Example 2 or DTT-gel of Example 3 was washed with 60% acetone-40% 0.05 M NaHCO$_3$ 1 mM in ethylenediaminetetraacetic acid (EDTA). The washed gel was then reacted with 0.3M 2,2'-dipyridyl disulfide.

EXAMPLE 5

Covalent Chromatographic Purification of Urease

Partially purified jack-bean urease in the amount of 1 g was added to 40 ml 0.1M Tris-HCl, pH 7.4 containing 1 mM EDTA and 5 mM dithiothreitol (DTT). The resulting suspension was stirred at 4° C. for 1 hour and then centrifuged to remove the particulate fraction. A volume of 5 ml of the cloudy supernatant was passed through a Sephadex G-50C 1×50 cm column which was equilibrated with 0.05 M Tris-HCl, pH 7.4 containing 0.5 mM EDTA. This procedure insured that any dithiothreitol present would be removed in order to prevent interference during the subsequent covalent chromatographic procedure.

A 5 ml volume of the DTT-free eluate was applied to a 0.5>20 cm column of the activated DS-gel of Example 4. The column was then washed with 0.05 M Tris-HCl, pH 7.4, containing 0.5 mM EDTA until the absorbance at 280 nm of the elulate was less than 0.1 and with 0.05 M Tris-HCl, pH 7.4 containing 0.05 mM EDTA and 0.05M NaCl until the absorbance was less than 0.02.

The enzyme urease was eluted from the column by 0.05 mM Tris-HCl, pH 7.4, containing 0.05 mM EDTA and 20 mM dithiothreitol (DTT). Urease activity was assayed by measuring the rate of disappearance of NADH absorbance at 340 nm through a glutamic dehydrogenase coupled reaction The substrate solution used in the reaction contained 0.05M Tris-HCl, pH 7.4; 0.5 mM EDTA; 1 mM ADP; 1 mM Alpha-ketoglutarate; 50 mM urea and 50U glutamic dehydrogenase. The assay was initiated by adding 5-10 microliters of enzyme solution to 2 ml of substrate solution. The results of the immobilization of the urease upon the column and the elution from the column are shown in FIG. 2.

Figure 2:
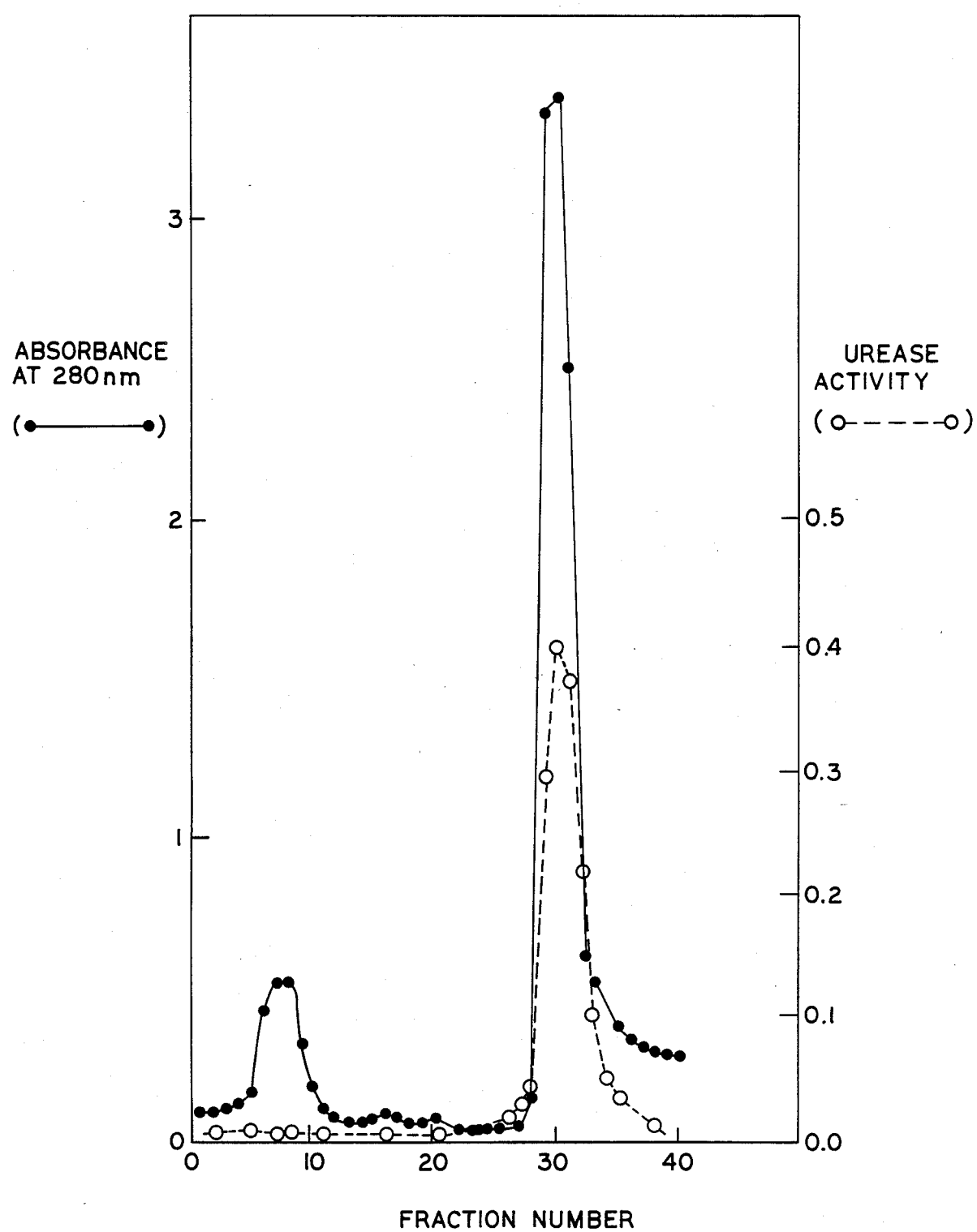
FIG. 2 is an elution curve showing the absorbance of various fractions of eluate during the purification of jack-bean urease by covalent chromatography.

From the solid curve of FIG. 2 it can be seen that most of the UV absorbing materials pass through the column unretarded. These materials were eluted in the first 11 fractions. Upon application of buffer containing a high concentration of NaCl, a small amount of additional UV absorbing material was eluted in fractions 15-20. The dotted line curve representing the urease activity shows that no urease activity was detected until DTT was applied to the column. After DTT was applied, starting at fraction 24, strong UV absorbing material was eluted in fractions 29-33, as is shown in the curve. The application of DTT released not only the enzyme but also 2-thiopyridone, which is also strongly absorbing at 280 nm. That the UV absorbing material constituted mostly 2-thiopyridone (approximately 90%) was established by dialysis of these fractions against 2000 ml 0.05 mM EDTA in 0.05M Tris-HCl, pH 7.4, which resulted in an average 34-fold reduction in their UV absorbance. Urease activity also increased at the same time as the increase in UV absorbance. A single passage of the enzyme solution through the activated thiol gel resulted in an 11-fold purification with 83% recovery of the total enzyme. The purified enzyme was found to have a specific activity of 770 units/mg.

Similar results can be obtained using the activated DTT-gel of Example 4.

The following example illustrates the reversible immobilization of a biologically active material by means of covalent linkage through a disulfide bridge to the activated thiol gel of the present invention. It should be pointed out that immobilization of a biologically active material for the purpose of providing such material in a form which is convenient to use requires that the disulfide bridge be formed utilizing a sulfhydryl group which is not essential to the activity of the biologically active material.

EXAMPLE 6

Reversible Immobilization of Beta-Galactosidase

Figure 3:
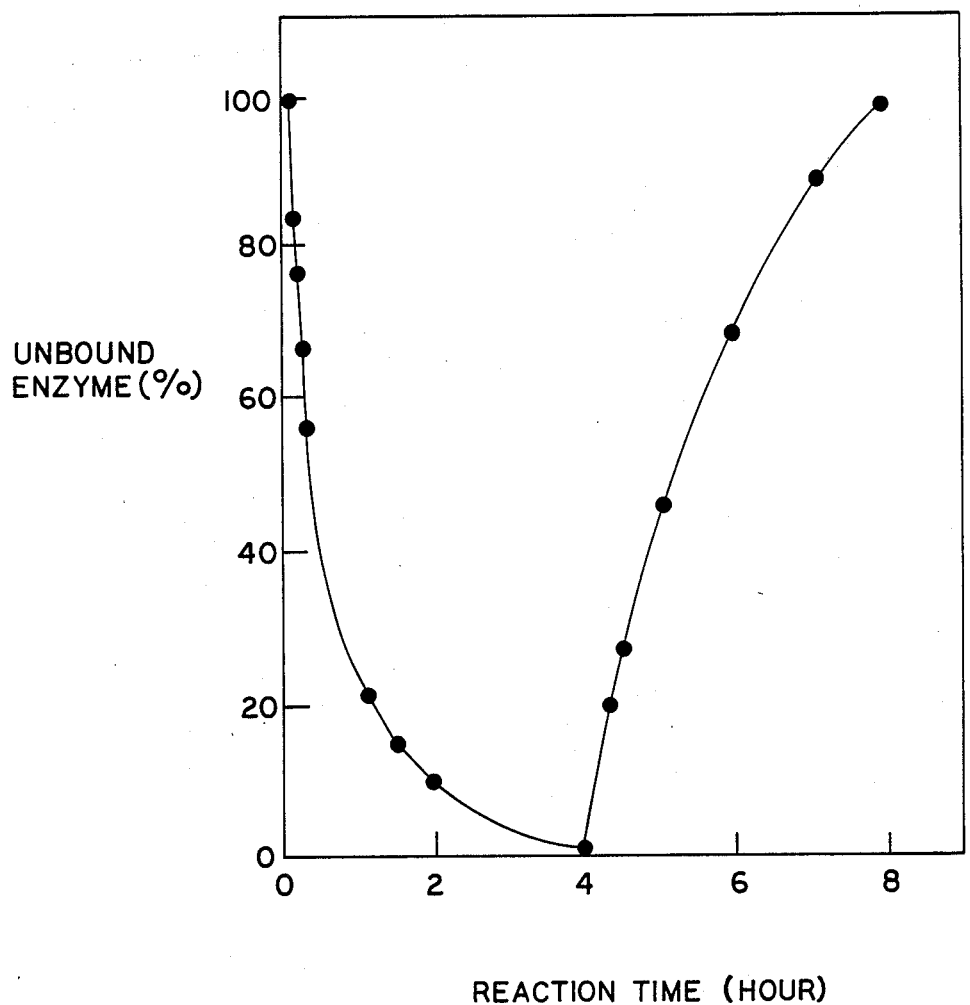
FIG. 3 is a reaction curve showing the course of the immobilization of *E. Coli* beta-galactosidase on 2,2'-dithiodipyridyl activated thiol (DTT) gel and the reversal thereof on the addition of dithiothreitol.

*E. Coli* beta-galactosidase in a quantity of 5 mg was dissolved in 10 ml of 0.1 M sodium phosphate buffer, 0.15 M in NaCl, pH 7.4. Wet activated DTT-gel prepared according to the procedure of Example 4 in a quantity of 2.5 g was added to the enzyme solution. The resulting suspension was stirred at room temperature. At timed intervals, 0.1 ml of the gel suspension was withdrawn and centrifuged at 2500 rpm for 1 minute. The supernatant was diluted 50× with phosphate buffer and 0.25 ml of the diluted supernatant was assayed for beta-galactosidase in 2 ml o-nitrophenyl-beta-D-galactopyranoside solution. After 4 hours incubation at room temperature total immobilization of the betagalactosidase with full activity was realized. At that time 20 mM DTT in 0.05M phosphate, pH 7.7, was mixed with the immobilized enzyme and samples were withdrawn and assayed for beta-galactosidase. As shown in FIG. 3, the activity of beta-galactosidase increased until at 8 hours reaction time a total recovery of enzyme was realized.

The foregoing description of the invention has been directed to particular preferred embodiments for purposes of explanation and illustration. It will be apparent, however, to those skilled in the art, that many modifications and changes in the methods and materials may be made without departure from the scope and spirit of the invention. For example, other biologically active ligands and other uses of the covalent chromatographic matrices of this invention may be used. Particular enzymes described have been chosen for convenience and are not intended to limit the scope of this invention. It is the applicant's intention in the following claims to cover all such equivalent modifications and variations as fall within the true spirit and scope of the invention.

What is claimed is:

1. A polymeric thiol gel of the formula
$$\text{(P)}-CH_2-S-CH_2-CH(OH)CH(OH)CH_2-SH$$
wherein (P)—$CH_2$— represents a polymeric substance.

2. A process for preparing polymeric thiol gel of the formula (P)—$CH_2$—S—$CH_2CH(OH)CH(OH)CH_2$—SH, wherein (P)—$CH_2$— represents a polymeric substance, comprising the steps of:

reacting a polymeric substance containing at least one —$CH_2$—OH group with 2-fluoro-1-methyl-pyridinium toleune-4-sulfonate in a polar organic solvent containing a base to form a polymeric activated gel wherein at least some of the hydroxyl groups of the polymeric substance containing —$CH_2$—OH groups have been converted to 1-methyl-2-pyridoxy groups; and reacting the resulting 1-methyl-2-pyridoxy substituted polymer with dithiothreitol to form a polymeric thiol gel wherein at least some of the —$CH_2$—OH groups of said polymeric substance containing —$CH_2$—OH groups have been replaced by —$CH_2$—S—$CH_2CH$—(OH)CH(OH)$CH_2$—SH groups.

3. A process according to claim 2 wherein said polymeric substance containing at least one —$CH_2OH$ group is a polysaccharide.

4. A process according to claim 2 wherein said polymeric substance containing at least one —$CH_2$—OH group is a dextran.

5. A process according to claim 2 wherein said polymeric substance containing at least one —$CH_2$—OH group is an agarose.

6. A process according to claim 2 wherein said polymeric substance containing at least one —$CH_2$-OH group is in the form of a gel.

7. A polymeric thiol gel prepared according to the process of claim 2.

8. A covalent chromatographic method for purifying a biogically active ligand containing a free sulfhydryl group which comprises:

reacting a polymeric substance containing a plurality of hydroxyl groups with 2-fluoro-1-methyl-pryridinium toluene-4-sulfonate in a polar organic solvent containing a base to form a polymeric activated gel wherein at least some of the hydroxyl groups of said polymeric substance have been converted to 1-methyl-2-pyridoxy groups;

reacting the resulting 1-methyl-pyridoxy substituted polymer with dithiothreitol to form a gel wherein said 1-methyl-2-pyridoxy groups have been converted to dithiothreityl groups;

reacting the resulting dithiothreityl substituted polymer with 2,2'-dipyridyl disulfide to form a 2-pyridyl disulfide gel wherein said dithiothreityl groups have been converted to the 2-pyridyl disulfide derivative;

contacting a mixture containing a biologically active ligand containing a free sulfhydryl group with said 2-pyridyl disulfide gel, whereby said ligand is covalently linked to said 2-pyridyl disulfide gel;

separating said covalently linked ligand from said mixture; and removing a purified ligand from said 2-pyridyl disulfide gel by treatment with a low molecular weight sulfhydryl group containing compound.

* * * * *